(12) United States Patent
Richon et al.

(10) Patent No.: US 7,879,865 B2
(45) Date of Patent: Feb. 1, 2011

(54) TREATMENT OF CANCER OF THE BRAIN USING HISTONE DEACETYLASE INHIBITORS

(75) Inventors: Victoria M. Richon, Rye, NY (US); Paul A. Marks, Washington, CT (US); Richard A. Rifkind, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 11/282,420

(22) Filed: Nov. 18, 2005

(65) Prior Publication Data
US 2006/0079551 A1 Apr. 13, 2006

Related U.S. Application Data

(62) Division of application No. 10/273,401, filed on Oct. 16, 2002, now abandoned.

(60) Provisional application No. 60/329,705, filed on Oct. 16, 2001.

(51) Int. Cl.
*A61K 31/52* (2006.01)
*A61K 31/16* (2006.01)

(52) U.S. Cl. .................................. 514/263.21; 514/616

(58) Field of Classification Search ............ 514/263.21, 514/263.2, 263.22, 316, 330, 352, 372, 616
See application file for complete search history.

(56) References Cited

U.S. PATENT DOCUMENTS

| | | | |
|---|---|---|---|
| 4,690,918 A | 9/1987 | Beppu et al. ............ 514/23 |
| 5,055,608 A | 10/1991 | Marks et al. |
| 5,175,191 A | 12/1992 | Marks et al. |
| 5,330,744 A | 7/1994 | Pontremoli et al. |
| 5,369,108 A * | 11/1994 | Breslow et al. ........ 514/263.21 |
| 5,608,108 A | 3/1997 | Marks et al. |
| 5,654,333 A | 8/1997 | Samid ................. 514/538 |
| 5,668,179 A | 9/1997 | Breslow et al. |
| 5,700,811 A | 12/1997 | Breslow et al. |
| 5,773,474 A | 6/1998 | Breslow et al. |
| 5,840,960 A | 11/1998 | Marks et al. |
| 5,932,616 A | 8/1999 | Breslow et al. |
| 6,087,367 A | 7/2000 | Breslow et al. |
| 6,231,880 B1 | 5/2001 | Perrine ................. 424/423 |
| 6,239,176 B1 | 5/2001 | Nudelman et al. ......... 514/547 |
| 6,262,116 B1 | 7/2001 | Pandolfi et al. ............ 514/557 |
| 6,451,334 B2 | 9/2002 | Perrine ................. 424/423 |
| 6,495,719 B2 | 12/2002 | Lan-Hargest et al. |
| 6,511,990 B1 * | 1/2003 | Breslow et al. ............ 514/314 |
| 6,656,905 B1 | 12/2003 | Mori et al. |
| RE38,506 E | 4/2004 | Breslow et al. ............ 514/316 |
| 6,905,669 B2 | 6/2005 | DiMartino ............. 424/9.1 |
| 6,905,699 B2 * | 6/2005 | Nakamura ............ 424/405 |
| 7,126,001 B2 | 10/2006 | Breslow et al. ............ 546/171 |
| 7,148,257 B2 | 12/2006 | Bacopoulos et al. ........ 514/616 |
| 7,199,134 B2 | 4/2007 | Breslow et al. ............ 514/312 |
| 2002/0061860 A1 | 5/2002 | Li et al. |
| 2002/0065282 A1 | 5/2002 | Georges et al. |
| 2002/0103192 A1 | 8/2002 | Curtin et al. |
| 2003/0082666 A1 | 5/2003 | Kammer et al. ........... 435/19 |
| 2003/0114525 A1 | 6/2003 | Kammer et al. ........... 435/19 |
| 2003/0161830 A1 | 8/2003 | Jackson et al. ........ 424/146.1 |
| 2003/0235588 A1 | 12/2003 | Richon et al. .......... 424/146.1 |
| 2004/0018968 A1 | 1/2004 | Sgouros et al. ............ 514/9 |
| 2004/0072735 A1 | 4/2004 | Richon et al. ............ 514/9 |
| 2004/0077591 A1 | 4/2004 | Dangond |
| 2004/0087657 A1 | 5/2004 | Richon et al. |
| 2004/0122101 A1 | 6/2004 | Miller et al. ............ 514/575 |
| 2004/0127522 A1 | 7/2004 | Chiao et al. ............ 514/352 |
| 2004/0127523 A1 | 7/2004 | Bacopoulos et al. ........ 514/352 |
| 2004/0132643 A1 | 7/2004 | Fojo et al. ............... 514/12 |
| 2004/0132825 A1 | 7/2004 | Richon et al. ............ 514/575 |
| 2004/0142859 A1 | 7/2004 | Steffan et al. |
| 2004/0167184 A1 | 8/2004 | Wiech et al. ............ 560/312 |
| 2005/0004007 A1 | 1/2005 | Grant et al. ............... 514/7 |
| 2006/0009526 A1 | 1/2006 | Richon et al. ............ 514/575 |
| 2006/0009527 A1 | 1/2006 | Richon et al. ............ 514/575 |
| 2006/0167103 A1 | 7/2006 | Bacopoulos et al. ........ 514/575 |

(Continued)

FOREIGN PATENT DOCUMENTS

EP 0931792 7/1999

(Continued)

OTHER PUBLICATIONS

Http://www.oncologychannel.com/braincanceer/types.shtml (2007).*

(Continued)

*Primary Examiner*—Kevin Weddington
(74) *Attorney, Agent, or Firm*—Ivor R. Elrifi, Esq.; Mintz, Levin, Cohn, Ferris, Glovsky, and Popeo, P.C.

(57) ABSTRACT

The present application is directed to a method of treating diseases of the central nervous system (CNS) comprising administering to a individual in need of treatment a therapeutically effective amount of an inhibitor of histone deacetylase. In particular embodiments, the CNS disease is a neurodegenerative disease. In further embodiments, the neurogenerative disease is an inherited neurodegenerative disease, such as those inherited neurodegenerative diseases which are polyglutamine expansion diseases. The individual can be a mammal such as a primate or human.

4 Claims, 2 Drawing Sheets

U.S. PATENT DOCUMENTS

| | | | |
|---|---|---|---|
| 2006/0276547 A1 | 12/2006 | Bacopoulos et al. | 514/575 |
| 2007/0060614 A1 | 3/2007 | Bacopoulos et al. | 514/315 |
| 2007/0190022 A1 | 8/2007 | Bacopoulos et al. | 424/85.1 |
| 2008/0119562 A1 | 5/2008 | Richon et al. | 514/616 |
| 2008/0227862 A1 | 9/2008 | Richon et al. | 514/616 |
| 2008/0249179 A1 | 10/2008 | Miller et al. | 514/575 |

FOREIGN PATENT DOCUMENTS

| | | |
|---|---|---|
| EP | 1123111 | 8/2001 |
| EP | 1170008 | 1/2002 |
| EP | 1174438 | 1/2002 |
| EP | 0547000 | 6/2003 |
| GB | 2 309 696 | 6/1997 |
| JP | 7-196686 | 8/1995 |
| JP | 11-302173 | 11/1999 |
| JP | 11-335375 | 12/1999 |
| JP | 2000-256194 | 9/2000 |
| JP | 2001/348340 | 12/2001 |
| JP | 2001-354694 | 12/2001 |
| WO | WO 90/09092 | 8/1990 |
| WO | WO 93/07148 | 4/1993 |
| WO | WO 95/31977 | 11/1995 |
| WO | WO 97/11366 | 3/1997 |
| WO | WO 97/35990 | 10/1997 |
| WO | WO 98/39965 | 9/1998 |
| WO | WO 98/40080 | 9/1998 |
| WO | WO 98/55449 | 12/1998 |
| WO | WO 00/08048 | 2/2000 |
| WO | WO 00/21979 | 4/2000 |
| WO | WO 00/71703 | 11/2000 |
| WO | WO 01/14581 | 3/2001 |
| WO | WO 01/16106 | 3/2001 |
| WO | WO 01/18045 | 3/2001 |
| WO | WO 01/18171 | 3/2001 |
| WO | WO 0118171 A2 * | 3/2001 |
| WO | WO 01/38322 | 5/2001 |
| WO | WO 01/42437 | 6/2001 |
| WO | WO 01/70675 | 9/2001 |
| WO | WO 02/07722 | 1/2002 |
| WO | WO 02/15921 | 2/2002 |
| WO | WO 02/22577 | 3/2002 |
| WO | WO 02/26696 | 4/2002 |
| WO | WO 02/26703 | 4/2002 |
| WO | WO 02/30879 | 4/2002 |
| WO | WO 02/46129 | 6/2002 |
| WO | WO 02/46144 | 6/2002 |
| WO | WO 02/50285 | 6/2002 |
| WO | WO 02/051842 | 7/2002 |
| WO | WO 02/055017 | 7/2002 |
| WO | WO 02/085400 | 10/2002 |
| WO | WO 02/090534 | 11/2002 |
| WO | WO 03/083067 | 10/2003 |
| WO | WO 2005/023179 | 3/2005 |

OTHER PUBLICATIONS

Furamai et al. (2001). *Proc. Natl. Acad. Sci. USA* 98: 87-92.
International Search Report for PCT/US02/33246, mailed Jul. 22, 2003.
Komatsu et al. (2001). *Cancer Res.* 61: 4459-4466.
Lee et al. (2001). *Cancer Res.* 61: 931-934.
Saito et al. (1999). *Proc. Natl. Acad. Sci. USA* 96: 4592-4597.
Su et al. (2000). *Cancer Res.* 60: 3137-3142.
Suzuki et al. (1999). *J. Med. Chem.* 42: 3001-3003.
Yoshida (1995). *Bioessays* 17: 423-430.
Arky et al., Physician's Desk Reference, Ed. 51:2198-2201, 1997.
Bates et al., "Polyglutamine Expansion and Huntington's Disease," Biochemical Society Transactions, 1998, vol. 26, No. 3, pp. 471-475.
Bates et al., "Symposium: Transgenic Models Of Neurodegeneration; Transgenic Mice In The Study Of Polyglutamine Repeat Expansion Diseases", Brain Pathology, vol. 8, 1998, pp. 699-714.
Bates et al., Transgenic Models of Huntington's Disease, Human Molecular Genetics, 1997, vol. 6, No. 10, Rev. Issue, pp. 1633-1637.
Butler et al., "Suberoylanilide Hydroxamic Acid, An Inhibitor Of Histone Deacetylase, Suppresses The Growth Of Prostate Cancer Cells In Vitro And In Vivo", Cancer Research, vol. 60, Sep. 15, 2000, pp. 5165-5170.
Cattaneo et al., "Loss Of Normal Huntingtin Function: New Developments In Huntington's Disease Research", Trends in Neurosciences, vol. 24, No. 3, Mar. 2001, pp. 182-188.
Cha, J., "Transcriptional Dysregulation In Huntington's Disease", TINS, vol. 23, No. 9, 2000, pp. 387-392.
Davies et al., "Formation Of Neuronal Intranuclear Inclusions Underlies The Neurological Dysfunction In Mice Transgenic For The HD Mutation", Cell, vol. 90, Aug. 8, 1997, pp. 537-548.
Difiglia et al., "Aggregation Of Huntingtin In Neuronal Intranuclear Inclusions And Dystrophic Neurites In Brain", Science, vol. 277, Sep. 26, 1997, pp. 1990-1993.
Dunah et al., "Sp1 and TAFII130 Transcriptional Activity Disrupted In Early Huntington's Disease", Science, vol. 296, Jun. 21, 2002, pp. 2238-2243.
Ferrante et al., "Neuroprotective Effects Of Creatine In A Transgenic Mouse Model Of Huntington's Disease", The Journal of Neuroscience, vol. 20, No. 12, Jun. 15, 2000, pp. 4389-4397.
Furumai et al., "FK228 (Depsipeptide) as a Natural Prodrug That Inhibits Class I Histone Deacetylases," Cancer Res., 62(17):4916-4921, 2002.
Gottlicher et al., "Valproic Acid Defines a Novel Class of HDAC Inhibitors Inducing Differentiation of Transformed Cells," The EMBO Journal, 2002, vol. 20, No. 24, pp. 6969-6978.
Gupta et al., "Characterization of a Phylotoxic Cyclotetrapeptide, a Novel Chiamydocin Analog, from Verticillum Coccosporum," (1994) Tetrahedron Letters, 35(33), 6009-6012.
Gurney, "The use of transgenic mouse models of amyotrophic lateral sclerosis in preclinical drug studies," J. Neurol. Sci., 152(Suppl. I):S67-S73, 1997.
Gutekunst et al., "Nuclear And Neuropil Aggregates In Huntington's Disease: Relationship To Neuropathology", The Journal of Neuroscience, vol. 19, No. 7, Apr. 1, 1999, pp. 2522-2534.
Han et al., "Apicidin, a histone deacetylase inhibitor, inhibits proliferation of tumor cells via induction of p21WAFI/Cip1 and gelsolin," Cancer Research, 60:6068-6074, 2000.
Hinnebusch et al., "The effects of short-chain fatty acids on human colon cancer cell phenotype are associated with histone hyperacetylation," J. Nutr., 132(5):1012-1017, 2002.
Hockly et al., "Environmental Enrichment Slows Disease Progression In R6/2 Huntington's Disease Mice", Ann. Neurol., vol. 51, 2002, pp. 235-242.
Hoffmann et al, "Fluorescence-labeled octapeptides as substrates for histone deacetylase," Bioconjugate Chem., 12:51-55, 2001.
Holbert et al., "The Gln-Ala Repeat Transcriptional Activator CA150 Interacts With Huntingtin: Neuropathologic And Genetic Evidence For A Role In Huntington's Disease Pathogenesis", PNAS, vol. 98, No. 4, Feb. 13, 2001, pp. 1811-1816.
Hughes et al., "Altered Transcription In Yeast Expressing Expanded Polyglutamine", PNAS, vol. 98, No. 23, Nov. 6, 2001, pp. 13201-13206.
Hughes et al., "Therapeutic Opportunities In Polyglutamine Disease", Nature Medicine, vol. 7, No. 4, Apr. 2001. pp. 419-423.
Hughes, R., "Polyglutamine Disease: Acetyltransferases Awry", Current Biology, vol. 12, Feb. 19, 2002, pp. R141-R143.
Jung et al., "Amide analogues of trichostatin A as inhibitors of histone deacetylase and inducers of terminal cell differentiation." J. Med. Chem., 42:4669-4679. 1999.
Jung et al., "Analogues of tricchostatin A and trapoxin B as histone inhibitors," Bioorgonic & Medicinal Chemistry Letters, 7:1655-1658, 1997.
Jung, "Inhibitors of histone deacetylase as new anticancer agents," Curr. Med. Chem., 8(12):1505-1511, 2001.
Kazantsev et al., "A Bivalent Huntinan Binding Peptide Suppresses Polyglutamine Aggregation And Pathogenesis In Drosophila", Nature Genetics, vol. 30, Apr. 2002, pp. 367-376.
Kazantsev et al., "Insoluable Detergent-Resistant Aggregates Form Between Pathological And Nonpathological Lengths Of Polyglutamine In Mammalian Cells", Proc. Natl. Acad. Sci. USA, vol. 96, Sep. 1999, pp. 11404-11409.

Kegel et al., "Huntingtin Is Present In the Nucleus, Interacts With The Transcriptional Corepressor C-terminal Binding Protein, And Represses Transcription", The Journal of Biological Chemistry, vol. 277, No. 9. Mar. 1, 2002, pp. 7466-7476.

Khoshnan et al., "Effects Of Intracellular Expression Of Anti-Huntingtin Antibodies Of Various Specificities On Mutant Huntingtin Aggregation And Toxicity", PNAS, vol. 99, No. 2, Jan. 22, 2002, pp. 1002-1007.

Kim et al., "Oxamflatin is a novel antitumor compound that inhibits mammalian histone deacetylase," Oncogene, 18:2461-2470,1999.

Kitazomo et al., "Low concentrations of the histone deacetylase inhibitor, depsipeptide (FR901228), increase expression of the Na+/I-symporter and iodine accumulation in poorly differentiated thyroid carcinoma cells," J. Clinical Endocrinology Metabolism, 86(7):3430-3435, 2001.

Kramer et al., "Histone Deacetylase As A Therapeutic Target", Trends in Endocrinology & Metabolism, vol. 12, No. 7, Sep. 2001, pp. 294-300.

Leoni, et al., "The Antitumor Histone Deacetylase Inhibitor Suberoylanilide Hydroxamic Acid Exhibits Antiinflammatory Properties Via Suppression of Cytokines," PNAS, Mar. 2002, vol. 99, No. 5, pp. 2995-3000.

Levy et al., Gamma Hydroxybutyrate in the Treatment of Schizophrenia, Psychiatry Research, 1983, vol. 9, No. 1, pp. 1-8.

Li et al., "Interaction Of Huntington Disease Protein With Transcriptional Activator Sp1", Molecular and Cellular Biology, vol. 22, No. 5, Mar. 2002, pp. 1277-1287.

Mai et al. "Binding mode analysis of 3-(4-Benzyol-1-methyl-1H2-pyrroly1)-N-hydroxy-2-propenamide: a new synthetic histone deacetylase inhibitor inducing histone hyperacetylation, growth inhibition and terminal cell differentiation" J. Med. Chem., 45(9):1778-1784, 2002.

Mangiarini et al., "Exon 1 Of The HD Gene With An Expanded CAG Repeat Is Sufficient To Cause A Progressive Neurological Phenotype In Transgenic Mice", Cell, vol. 87, Nov. 1, 1996, pp. 493-506.

Mangiarini et al., "Instability of Highly Expanded CAG Repeats in Mice Transgenic for the Huntington's Disease Mutation," Nature Genetics, Feb. 1997, vol. 15, No. 2, pp. 197-200.

Margolis et al., "Expansion Explosion: New Clues To The Pathogenesis Of Repeat Expansion Neurodegenerative Diseases", Trends in Molecular Medicine, vol. 11, No. 7, Nov. 2001, pp. 479-482.

Marks et al.; "Histone Deacetylase Inhibitors: Inducers of Differentiation or Apoptosis of Transformed Cells"; Journal of the National Cancer Institute; vol. 92, No. 15, Aug. 2, 2000; pp. 1210-1216.

Marks, et al., "Histone Deacetylase Inhibitors as New Cancer Drugs", Oncology, vol. 13, 2001, pp. 477-483.

Marsh et al.; "Expanded Polyglutamine Peptides Alone Are Intrinsically Cytotoxic and Cause Neurodegeneration in Drosophila", Human Molecular Genetics, vol. 9. No. 1; 2000; pp. 13-25.

Massa et al., "3-(4-Aroyl-1H-pyrrol-2-yl)-N-hydroxy-2-propenamides, a new class of synthetic Histone deacetylase inhibitors," J. Med. Chem., 44:2069-2072, 2001.

McCampbelL et al., "CREB-Binding Protein Sequestration By Expanded Polyglutamine", Human Molecular Genetics, vol. 9, No. 14, 2000, pp. 2197-2202.

McCampbell et al., "Histone Deacetylase Inhibitors Reduce Polyglutamine Toxicity," PNAS, Dec. 2001, vol. 98, No. 26, pp. 15179-15184.

McCampbell et al., "Polyglutamine And CBP: Fatal Attraction?", Nature Medicine, vol. 7, No. 5, May 2001, pp. 528-530.

Meyer et al., "Acute neuronal apoptosis in a rat model of multiple sclerosis," J. Neurosci., 21:6214-6220, 2001.

Mucke et al., "High-level neuronal expression of Aβ1-42 in wild-type human amyloid protein precursor transgenic mice: synaptotxicity without plaque formation," J. Neuroscience 20:4050-4058, 2000.

Nagai et al., "Rats expressing human cytosolic copper-zinc superoxide diimutase transgenes with amyotrophic lateral sclerosis: associated mutations develop motor neuron disease," J. Neurosci. 21:9246-9254, 2001.

Nancey et al., "Butyrate strongly inhibits in vitro stimulated release of cytokines in blood," Dig. Dis. Sci., 47:921-928, 2002.

Nucifora, Jr. et al., "Interference By Huntingtin And Atrophin-1 With CBP-Mediated Transcription Leading to Cellular Toxicity", Science, vol. 291, Mar. 23, 2001, pp. 2423-2428.

Pandolfi, P., "Histone Deacetylases And Transcriptional Therapy With Their Inhibitors", Cancer Chemother. Phannacol., vol. 48 (Suppl. I), 2001, pp. 517-S19.

Paulson, H., "Human Genetics '99: Trinucleotide Repeats Protein Fate In Neurodegenerative Proteinopathies: Polyglutamine Diseases Join The (Mis)Fold", Am. J. Hum. Genet., vol. 64, 1999, pp. 339-345.

Perutz, M., "Glutamine Repeats And Neurodegenerative Diseases: Molecular Aspects", TIBS, vol. 24, Feb. 1999, pp. 58-63.

Peters et al., "Nuclear Targeting Of Mutant Huntingtin Increases Toxicity", Molecular and Cellular Neuroscience, vol. 14, 1999, pp. 121-128.

Petersen et al., "Review: Recent Advances On The Pathogenesis Of Huntington's Disease", Experimental Neurology, vol. 157, 1999, pp. 1-18.

Phiel et al., "Histone Deacetylase Is A Direct Target Of Valproic Acid, A Potent Anticonvulsant, Mood Stabilizer, and Teratogen", The Journal of Biological Chemistry, vol. 276, No. 39, Sep. 28, 2001, pp. 36734-36741.

Pompl et al., "Caspase gene expression in the brain as a function of the clinical progression of Alzheimer disease," Arch. Neural., 60:369-376, 2003.

Price and Sisodia, "Mutant genes in familial Alzheimer's disease and transgenic models," Ann. Rev. Neurosci., 21:479-505, 1998.

Reddy et al., "Recent Advances In Understanding The Pathogenesis Of Huntington's Disease", TINS, vol. 22, No. 6, 1999, 248-255.

Richon et al., "A Class Of Hybrid Polar Inducers Of Transformed Cell Differentiation Inhibits Histone Deacetylases", Cell Biology, Proc. Natl. Acad. Sci., USA, vol. 95, Mar. 1998, pp. 3003- 3007.

Richon et al., "Histone Deacetylase Inhibitor Selectively Induces p21WAFI Expression And Gene-Associated Histone Acetylation", PNAS, vol. 97, No. 18, Aug. 29, 2000, pp. 10014-10019.

Saemann et al., "Anti-inflammatory effects of sodium butyrate on human monocytes: potent inhibition of IL-12 and up-regulation of IL-10 production," FASEB J., 14:2380-2382, 2000.

Saratikov et al., "Action of Lithium Hydroxybutryate on Electroencephalographic Effects of Amphetamine," Bulletin of Experimental Biology and Medicine (English Translation 1982), vol. 94, No. 7, pp. 907-910.

Saudou et al., "Huntingtin Acts In The Nucleus To Induce Apoptosis But Death Does Not Correlate With The Formation Of Intranuclear Inclusions", Cell, vol. 95, Oct. 2, 1998, pp. 55-66.

Saunders et al., "Histone deacetylase inhibitors as potential anti-skin cancer agents," Cancer Res., 59:399-409, 1999.

Scherzinger et al., "Huntingtin-Encoded Polyglutamine Expansions Form Amyloid-like Protein Aggregates In Vitro And In Vivo", Cell, vol. 9, Aug. 8, 1997, pp. 549-558.

Shimohata et al., "Expanded Polyglutamine Stretches Interact With TAFII 130, Interfering With CREB-Dependent Transcription", Nature Genetics, vol. 26, Sep. 2000, pp. 29-36.

Sieradzan et al., "Huntington's Disease Intranuclear Inclusions Contain Truncated, Ubiquitinated Huntingtin Protein", Experimental Neurology, vol. 156, 1999, pp. 92-99.

Sipione et al., "Early Transcriptional Profiles In Huntingtin-Inducible Striatal Cells By Microarray Analyses", Human Molecular Genetics, vol. 11, No. 17, 2002, pp. 1953-1965.

Smith et al., "Inhibition Of Polyglutamine Aggregation In R6/2 HD Brain Slices-Complex Dose-Response Profiles", Neurobiology of Disease, vol. 8, 2001, pp. 1017-1026.

Steffan et al., "Histone Deacetylase Inhibitors Arrest Polyglutamine-dependent Neurodegeneration in Drosophila," Nature, vol. 413, Oct. 2001, pp. 739-743.

Steffan et al., "The Huntington's Disease Protein Interacts with p53 and CREB-binding Protein and Represses Transcription," PNAS, vol. 97. No. 12, Jun. 2000, pp. 6763-6768.

Takahashi et al., "Selective Inhibition of IL-2 Gene Expression by Trichostatin A, a Potent Inhibitor of Mammalian Histone Deacetylase", May, 1996, The Journal of Antibiotics, vol. 49, No. 5, pp. 453-457.

Uesato et al, "Novel Histone Deacetylase Inhibitors: N-Hydroxycarboxamides Possessing A Terminal Bicyclic Aryl Group", Bioorganic & Medicinal Chemistry Letters. vol. 12, 2002, pp. 1347-1349.

Vigushin and Coombes, "Histone deacetylase inhibitors in cancer treatment," Anticancer Drugs, 13(1):1-13, 2002.

Vigushin et al., "Trichostatin A is a histone deacetylase inhibitor with potent antitumor activity against breast cancer in vivo," Clinical Cancer Research, 7:971-976, 2001.

Wyttenbach et al., "Polyglutamine Expansions Cause Decreased CRE-Mediated Transcription And Early Gene Expression Changes Prior To Cell Death In An Inducible Cell Model of Huntington's Disease", Human Molecular Genetics, vol. 10, No. 17, 2001, pp. 1829-1845.

Yamano et al., "Amplification of transgene expression in vitro and in vivo using a novel inhibitor of histone deacetylase," Mol. Ther., 1(6):574-580 2000.

Yang et al. "Aggregated Polyglutamine Peptides Delivered To Nuclei Are Toxic To Mammalian Cells", Human Molecular Genetics, vol. 11, No. 23, 2002, pp. 2905-2917.

Zoghbi et al., "Glutamine Repeats And Neurodegeneration", Annual Rev. Neurosci., vol. 23, 2000, pp. 217-247.

"Aton Pharma, Inc. Appoints Judy H. Chiao, M.D., as Vice President, Oncology Clinical Research and Development", Sep. 20, 2002.

"Aton Pharma, Inc. Reports on Phase I Trial of SAHA", Aug. 14, 2002.

Adams and Elliott (2000). Oncogene 19: 6687-6692.

Adhikari, D et al. (1998). Proceedings of the American Association for Cancer Research Annual Meeting 39: 312, Abstract 2130.

Alexandrov, I et al. (1998). FEBS Letters 434: 209-214.

Almenara, J et al. (2002). Leukemia 16: 1331-1343.

Amin HM et al. (2001). British Journal of Haematology 115: 287-297.

Andrews et al. (2000). Intl. J. Parasitol. 30: 761-768.

Archer et al. (1998). Proc. Natl. Acad. Sci. USA 95: 6791-6796.

Bates et al. (1999). Proc. American Society of Clinical Oncology 18: 180a, Abstract No. 693.

Benoit, NE et al. (1996). Immunopharmacology 35: 129-139.

Bode, J et al. (1982). Journal of Interferon Research 2: 159-166.

Buckley, AR et al. (1996). Cell Growth & Differentiation 7: 1713-1721.

Buckley, AR et al. (1997). Proc. American Association for Cancer Research Annual 38: 193, Abstract No. 1294.

Butler et al. (2001). *Clinical Cancer Res.* 7: 962-970.

Butler et al. (2002). *Proc. Natl. Acad. Sci. USA* 99: 11700-11705.

Byrd, JC et al. (1999). Blood 94: 1401-1408.

Cao et al.(2001). Am. J. Respir. Cell Mol. Biol., 25:562-8.

Carducci, MA et al. (2001). Clinical Cancer Research 7: 3047-3055.

Coffey et al. (2000). *Medical and Pediatric Oncology 35*: 577-581.

Coffey et al. (2001). *Cancer Res. 61*: 3591-3594.

Cohen et al. (1999). *Anticancer Res. 19*: 4999-5005.

Cohen et al. (2002). *Anticancer Res. 22*: 1497-1504.

Curtin (2002). Exp. Opin. Ther. Patents 12: 1375-1384.

Dear, AE et al. (2000). Biochimica et Biophysics Acta 1492:, 15-22.

Dhordain, P et al. (1998). Nucleic Acids Research 26: 4645-4651.

Dressel (2000). *Anticancer Res. 20*: 1017-1022.

Fillppovich, I et al. (1994). 198: 257-265.

Finnin et al. (1999). Nature 401: 188-193.

Foss, FM et al. (1993). Blood 82: Suppl. 1, 564A, Abstract No. 2239.

Foster at al. (1997). Invest. New Drugs 15: 187-194.

Gelmetti, V et al. (1998). Molecular and Cellular Biology 18: 7185-7191.

Gerbitz (1999). Oncogene 18: 1745-1753.

Gilbert, J et al. (2001). Clinical Cancer Research 7: 2292-2300.

Gore and Carducci (2000). Exp. Opin. Invest. Drugs 9: 2923-2934.

Grunstein (1997). *Nature 389*: 349-352.

Harris, NL et al. (1994). Blood 84: 1361-1392.

He et al. (2001). *J. Clin. Investigation 108*: 1321-1330.

Huang and Pardee (2000). Molecular Medicine 6: 849-866.

Johnstone, R. (2002). Nature Reviews Drug Discovery 1: 287-299.

Kelly et al. (2001). Proc. American Society of Clinical Oncology 20: 87a, Abstract No. 344.

Kim et al. (1999). *Oncogene 18*: 2461-2470.

Kohge et al. (1998). *Biochem. Pharmacol. 56*: 1359-1364.

Kosugi et al. (2001). Jpn. J. Cancer Res. 92: 529-536.

Kouraklis and Theocharis (2002). *Curr. Med. Chem.-Anti-Cancer Agents 2*: 477-484.

Kurita-Ochiai, T et al. 1998. Infection and Immuity 66: 2587-2594.

Lin et al. (1998). *Nature 391*: 811-814.

Liu, Z et al. (1998). Journal of Cancer Research and Clinical Oncology 124: 541-548.

Madisen, L et al. (1998). 18: 6281-6292.

Mai et al. (2001). *OPPI Briefs 33*: 391-394.

Marks et al. (2001). Clinical Cancer Res. 7: 759-760.

Marks et al. (2001). Nature Reviews 1: 194-202.

Munster et al. (2001). Cancer Res. 61: 8492-8497.

Niitsu, N et al. (2000). Molecular Pharmacology 58: 27-36.

O'Connor et al. (2001). Journal of the American Society of Hematology 611a, Abstract No. 2562.

Orr, D et al. (2000). ASCO Annual Meeting, Abstract No. 763. Phase I clinical trial of oral suberoylanilide hydroxamic acid—SAHA (msk390) in patients with advanced solid tumors and hematologic malignancies; first patient dosed in Aug. 2001 at Memorial Sloan Kettering Cancer Center. SAHA gelatin capsules containing SAHA and excipients were administered to patients. The SAHA was prepared according to methods in Example 1 of U.S. Appl. No. 10/379,149.

Piekarz et al. (2001). Blood 98: 2865-2868.

Polack, A et al. (1993). The EMBO Journal 12: 3913-3920.

Prakash et al. (2001). Invest. New Drugs 19: 1-11.

Qui et al. (2000). *Mol. Biol. Cell 11*: 2069-2083.

Rezuke, WN et al. (1997). Clinical Chemistry 43: pp. 1814-1823.

Rha et al. (1993). J. Korean Med. Sci. 8:251-256.

Richon and O'Brien (2002). *Clinical Cancer Res. 8*: 662-664.

Richon et al. (1996). *Proc. Natl. Acad. Sci. USA 93*: 5705-5708.

Rifkind et al. (2002). 224th ACS National Meeting, Boston, MA, Abstract No. 226.

Rottleb, C et al. (199). International Journal of Cancer 62: 697-702.

Rottleb, C et al. (1996). International Journal of Cancer 67: pp. 724-729.

Rubartelli et al. (1995). Cancer Research: 55: 675-680.

Rubio, MA et al. (1995). Blood 86: 3715-3724.

Sandor et al. (2002). Clincal Cancer Research 8: 718-728.

Stowell et al. (1995). J. Med. Chem. 38: 1411-1413.

Summerhayes, M. (2001). J. Oncol. Pharm. Prac. 7: 107-125.

Van Lint et al. (1996). *Gene Expression 5*: 245-253.

Vigushin, D. (2002). Current Opin. Invest. Drugs 3: 1396-1402.

Vrana et al. (1999). *Oncogene 18*: 7016-7025.

Waheed et al. (2000). Proceedings of the American Association for Cancer Research, 41:808, Abstract 5135.

Warrell et al. (1998). J. Natl. Cancer Institute 90: 1621-1625.

Watanabe, M et al. (1990). Cancer Research 50: 3245-3248.

Webb et al. (1999). J. Biol. Chem. 274: 14280-14287.

Weiser et al. (2001). J. Immunother., 24:151-61.

Wu et al. (2001). Oncogene 20(2): 240-251, Abstract, Database CAPLUS on STN, Acc. No. DN134:293668.

Yoshida et al. (1990). *J. Biol. Chem. 265*: 17174-17179.

Yu, C et al. (2001). Cancer Research 63: 2118-2126.

Zhang, M et al. (1998). Cell Stress & Chaperones 3: No. 1, 57-66.

Zhou et al. (1999). Gene 233: 13-19.

Zhou et al. (2000). Proc. Natl. Acad. *Sci. USA 97*: 1056-1061.

Zhou et al. (2000). Proc. Natl. Acad. Sci. USA 97: 14329-14333.

Zhou et al. (2001). Proc. Natl. Acad. Sci. USA 98: 10572-10577.

International Preliminary Examination Report for PCT/US03/06451, mailed Aug. 3, 2004.

International Search Report for PCT/US03/06451, mailed Oct. 27, 2003.

International Search Report for PCT/USO4/27943, mailed Mar. 7, 2005.

Supplementary European Search Report for PCT/US03/06451, mailed Aug. 21, 2007.

U.S. Appl. No. 12/077,396, filed Mar. 18, 2008, Miller et al.

Supplementary European Search Report for PCT/US02/33246 dated Mar. 15, 2007.

Levin, Victor A., "Relationship of Octanol/Water Partition Coefficient and Molecular Weight to Rat Brain Capillary Permeability", *J. Med. Chem.*, 23, 682-684 (1980).

Lau et al., "Differentiation Induction in Medulloblastoma Cell Lines by Phenylbutyrate", *Proceedings of the American Association for Cancer Research*, vol. 39, Mar. 1998.

* cited by examiner

TREATMENT OF CANCER OF THE BRAIN USING HISTONE DEACETYLASE INHIBITORS

RELATED APPLICATIONS

This application is a divisional of U.S. application Ser. No. 10/273,401 filed on Oct. 16, 2002, abandoned, which claims the benefit of U.S. Provisional Application No. 60/329,705 filed on Oct. 16, 2001. The entire teachings of the above-referenced applications are incorporated herein by reference.

BACKGROUND OF THE INVENTION

Compounds which inhibit histone deacetylase (HDACs) have been shown to cause growth arrest, differentiation and/or apoptosis of many different types of tumor cell in vitro and in vivo. HDACs catalyze the removal of the acetyl group from the lysine residues in the N-terminal tails of nucleosomal core histones resulting in a more compact chromatin structure, a configuration that is generally associated with repression of transcription. These HDAC inhibitors fall into four general classes: 1) short-chain fatty acids (e.g., 4-phenylbutyrate and valproic acid); hydroxamic acids (e.g., SAHA, Pyroxamide, trichostatin A (TSA), oxamflatin and CHAPs, such as, CHAP1 and CHAP 31); 3) cyclic tetrapeptides (Trapoxin A and Apicidin); 4) benzamides (e.g. MS-275); and other compounds such as Scriptaid. Examples of such compounds can be found in U.S. Pat. No. 5,369,108, issued on Nov. 29, 1994, U.S. Pat. No. 5,700,811, issued on Dec. 23, 1997, and U.S. Pat. No. 5,773,474, issued on Jun. 30, 1998 to Breslow et al., U.S. Pat. No. 5,055,608 issued on Oct. 8, 1991, and U.S. Pat. No. 5,175,191, issued on Dec. 29, 1992 to Marks et al., as well as, Yoshida, M., et al., Bioassays 17, 423-430 (1995), Saito, A., et al., PNAS USA 96, 4592-4597, (1999), Furamai R. et al., PNAS USA 98 (1), 87-92 (2001), Komatsu, Y., et al., Cancer Res. 61(11), 4459-4466 (2001), Su, G. H., et al., Cancer Res. 60, 3137-3142 (2000), Lee, B. I. et al., Cancer Res. 61(3), 931-934, Suzuki, T., et al., J. Med. Chem. 42(15), 3001-3003 (1999) and published PCT Application WO 01/18171 published on Mar. 15, 2001 to Solan-Kettering Institute for Cancer Research and The Trustees of Columbia University the entire content of all of which are hereby incorporated by reference.

Preferred hydroxanic acid based HDAC inhibitors are suberoylanilide hydroxamic acid (SAHA) and pyroxamide. SAHA has been shown to bind directly in the catalytic pocket of the histone deacetylase enzyme. SAHA induces cell cycle arrest, differentiation and/or apoptosis of transformed cells in culture and inhibits tumor growth in rodents. SAHA is effective at inducing these effects in both solid tumors and hematological cancers. It has been shown that SAHA is effective at inhibiting tumor growth in animals with no toxicity to the animal. The SAHA-induced inhibition of tumor growth is associated with an accumulation of acetylated histones in the tumor. SAHA is effective at inhibiting the development and continued growth of carcinogen-induced (N-methylnitrosourea) mammary tumors in rats. SAHA was administered to the rats in their diet over the 130 days of the study. Thus, SAHA is a nontoxic, orally active antitumor agent whose mechanism of action involves the inhibition of histone deacetylase activity.

SUMMARY OF THE INVENTION

It has been surprisingly discovered that certain HDAC inhibitors, for example, SAHA and pyroxamide can cross the blood brain barrier at sufficient amounts to significantly inhibit HDAC activity causing the accumulation of acetylated histones in the brain. This discovery therefore provides for the use of HDAC inhibitors in the treatment of disorders of the central nervous system including cancer of the brain and neurodegenerative diseases.

The present application is directed to a method of treating diseases of the central nervous system (CNS) comprising administering to a individual in need of treatment a therapeutically effective amount of an inhibitor of histone deacetylase. In particular embodiments, the CNS disease is a neurodegenerative disease. In further embodiments, the neurogenerative disease is an inherited neurodegenerative disease, such as those inherited neurodegenerative diseases which are polyglutamine expansion diseases.

The individual can be a mammal such as a primate or human.

DETAILED DESCRIPTION OF THE INVENTION

The present application is directed to a method of treating diseases of the central nervous system (CNS) comprising administering to a individual in need of treatment a therapeutically effective amount of an inhibitor of histone deacetylase. In particular embodiments, the CNS disease is a neurodegenerative disease. In further embodiments, the neurogenerative disease is an inherited neurodegenerative disease, such as those inherited neurodegenerative diseases which are polyglutamine expansion diseases. In a preferred embodiment, the neurodegenerative disease is Huntington's disease.

The individual can be a mammal such as a primate or human.

Therapeutically effective amount as that term is used herein refers to an amount which elicits the desired therapeutic effect. The therapeutic effect is dependent upon the disease being treated. As such, the therapeutic effect can be a decrease in the severity of symptoms associated with the disease and/or inhibition (partial or complete) of progression of the disease. The amount needed to elicit the therapeutic response can be determined based on the age, health, size and sex of the patient. Optimal amounts can also be determined based on monitoring of the patient's response to treatment.

Generally, diseases of the central nervous system, are referred to as neurodegenerative, indicating that they are characterized by gradually evolving, relentlessly progressive neuronal death occurring for reasons that are still largely unknown. The identification of these diseases depends upon exclusion of such possible causative factors as infections, metabolic derangements, and intoxications. A considerable proportion of the disorders classed as neurogenerative are genetic, with either dominant or recessive inheritance. Others, however, occur only sporadically as isolated instances in a given family. Classification of the degenerative diseases cannot be based upon any exact knowledge of cause or pathogenesis; their subdivision into individual syndromes rests on descriptive criteria based largely upon neuropathologic and clinical aspects. This group of diseases presents as several distinct clinical syndromes, the recognition of which can assist the clinician in arriving at a diagnosis.

However, research in the past decade has uncovered a new classification of inherited neurodegenerative diseases, the polyglutamine (polyQ) expansion diseases. In each, the underlying mutation is an expansion of a CAG trinucleotide repeat that encodes polyQ in the respective disease protein. All are progressive, ultimately fatal disorders that typically begin in adulthood and progress over 10 to 30 years. The clinical features and pattern of neuronal degeneration differ among the diseases, yet increasing evidence suggests that polyQ diseases share important pathogenic features. In particular, abnormal protein conformations(s) promoted by polyQ expansion seem to be central to pathogenesis. This class of PolyQ expansion neurodegenerative disease are Huntington's Disease (HD), Dentatorubralpallidoluysian atrophy (DRPLA), spinal and bulbar muscular atrophy (SBMA), and five spinocerebellar ataxias (SCA1, SCA2, SCA3/MJD (Machado-Joseph Disease), SCA6 and SCA7). These diseases are listed in the general listing of neurodegenrative disease below. Many of these diseases not yet connected with PolyQ expansion are thought to result from abnormal protein folding and aggregation (e.g., Alzheimer's disease).

Generally, neurodegenerative diseases can be grouped as follows:
I. Disorders characterized by progressive dementia in the absence of other prominent neurologic signs.
  A. Alzheimer's disease
  B. Senile dementia of the Alzheimer type
  C. Pick's disease (lobar atrophy)
II. Syndromes combining progressive dementia with other prominent neurologic abnormalities
  A. Mainly in adults
    1. Huntington's disease
    2. Multiple system atrophy combining dementia with ataxia and/or manifestations of Parkinson's disease
    3. Progressive supranuclear aplsy (Steel-Richardson-Olszewski)
    4. Diffuse Lewy body disease
    5. Corticodentatonigral degeneration
  B. Mainly in children or young adults
    1. Hallervorden-Spatz disease
    2. Progressive familial myoclonic epilepsy
III. Syndromes of gradually developing abnormalities of posture and movement
  A. Paralysis agitans (Parkinson's disease)
  B. Striatonigral degeneration
  C. Progressive supranuclear palsy
  D. Torsion dystonia (torsion spasm; dystonia musculorum deformans)
  E. Spasmodic torticollis and other dyskinesis
  F. Familial tremor
  G. Gilles de la Tourette syndrome
IV. Syndromes of progressive ataxia
  A. Cerebellar degenerations
    1. Cerebellar cortical degeneration
    2. Olivopontocerebellar atrophy (OPCA)
  B. Spinocerebellar degeneration (Friedreich's atazia and related disorders)
V. Syndrome of central autonomic nervous system failure (Shy-Drager syndrome)
VI. Syndromes of muscular weakness and wasting without sensory changes (motor neuron disease
  A. Amyotrophic lateral sclerosis
  B. Spinal muscular atrophy
    1. Infantile spinal muscular atrophy (Werdnig-Hoffman)
    2. Juvenile spinal muscular atrophy (Wohlfart-Kugelberg-Welander)
    3. Other forms of familial spinal muscular atrophy
  C. Primary lateral sclerosis
  D. Hereditary spastic paraplegia
VII. Syndromes combining muscular weakness and wasting with sensory changes (progressive neural muscular atrophy; chronic familial polyneuropathies)
  A. Peroneal muscular atrophy (Charcot-Marie-Tooth)
  B. Hypertrophic interstitial polyneuropathy (Dejerine-Sottas)
  C. Miscellaneous forms of chronic progressive neuropathy
VIII. Syndromes of progressive visual loss
  A. Pigmentary degeneration of the retina (retinitis pigmentosa)
  B. Hereditary optic atrophy (Leber's disease)

HDAC inhibitors suitable for use in the invention include, but are not limited to the following specific structures:

-continued

-continued

Further, HDAC inhibitors which can be useful can include the four general classes described above: 1) short-chain fatty acids (e.g., 4-phenylbutyrate and valproic acid); hydroxamic acids (e.g., SAHA, Pyroxamide, trichostatin A (TSA), oxamflatin and CHAPs, such as, CHAP1 and CHAP 31); 3) cyclic tetrapeptides (Trapoxin A and Apicidin; 4) benzamides (e.g., MS-275); and other compounds such as Scriptaid. Examples of such compounds can be found in U.S. Pat. Nos. 5,369,108, issued on Nov. 29, 1994, 5,700,811, issued on Dec. 23, 1997, and 5,773,474, issued on Jun. 30, 1998 to Breslow et al., U.S. Pat. Nos. 5,055,608, issued on Oct. 8, 1991, and 5,175,191, issued on Dec. 29, 1992 to Marks et al., as well as, Yoshida, M., et al., Bioassays 17, 423430 (1995), Saito, A., et al., PNAS USA 96, 4592-4597, (1999), Furamai R. et al., PNAS USA 98 (1), 87-92 (2001), Komatsu, Y., et al., Cancer Res. 61(11), 4459-4466 (2001), Su, G. H., et al., Cancer Res. 60, 3137-3142 (2000), Lee, B. I. et al., Cancer Res. 61(3), 931-934, Suzuki, T., et al., J. Med. Chem. 42(15), 3001-3003 (1999) and published PCT Application WO 01/18171 published on Mar. 15, 2001 to Sloan-Kettering Institute for Cancer Research and The Trustees of Columbia University the entire content of all of which are hereby incorporated by reference.

EXPERIMENTAL METHODS

Figure 1:
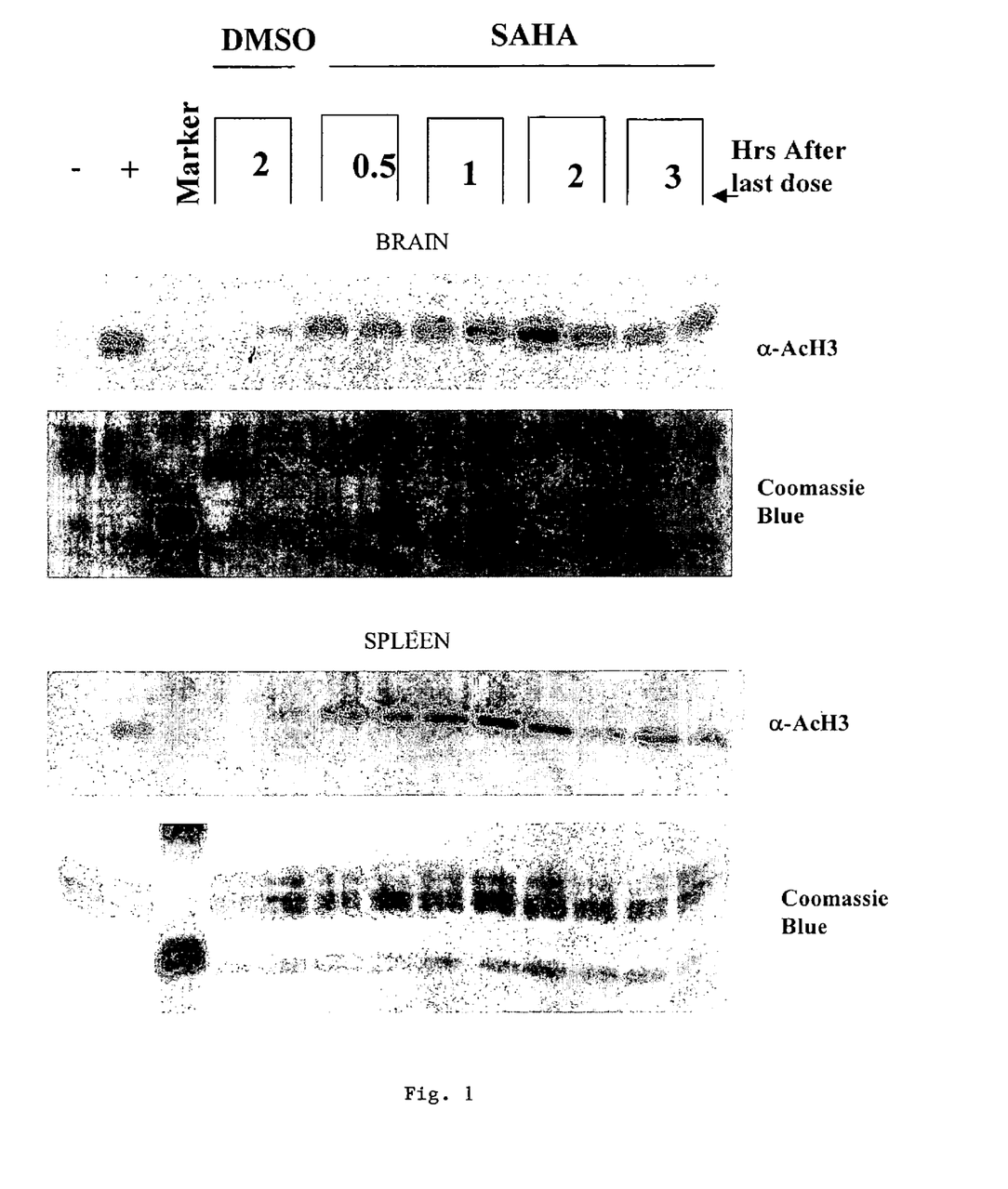
FIG. 1 is a scan of a Western blot and Coomassie stained gel indicating levels of acetylated histone ($\alpha$AcH3) at the indicated timepoints following treatment with vehicle (DMSO) or three doses of SAHA (100 mg/kg/hr).
Figure 2:
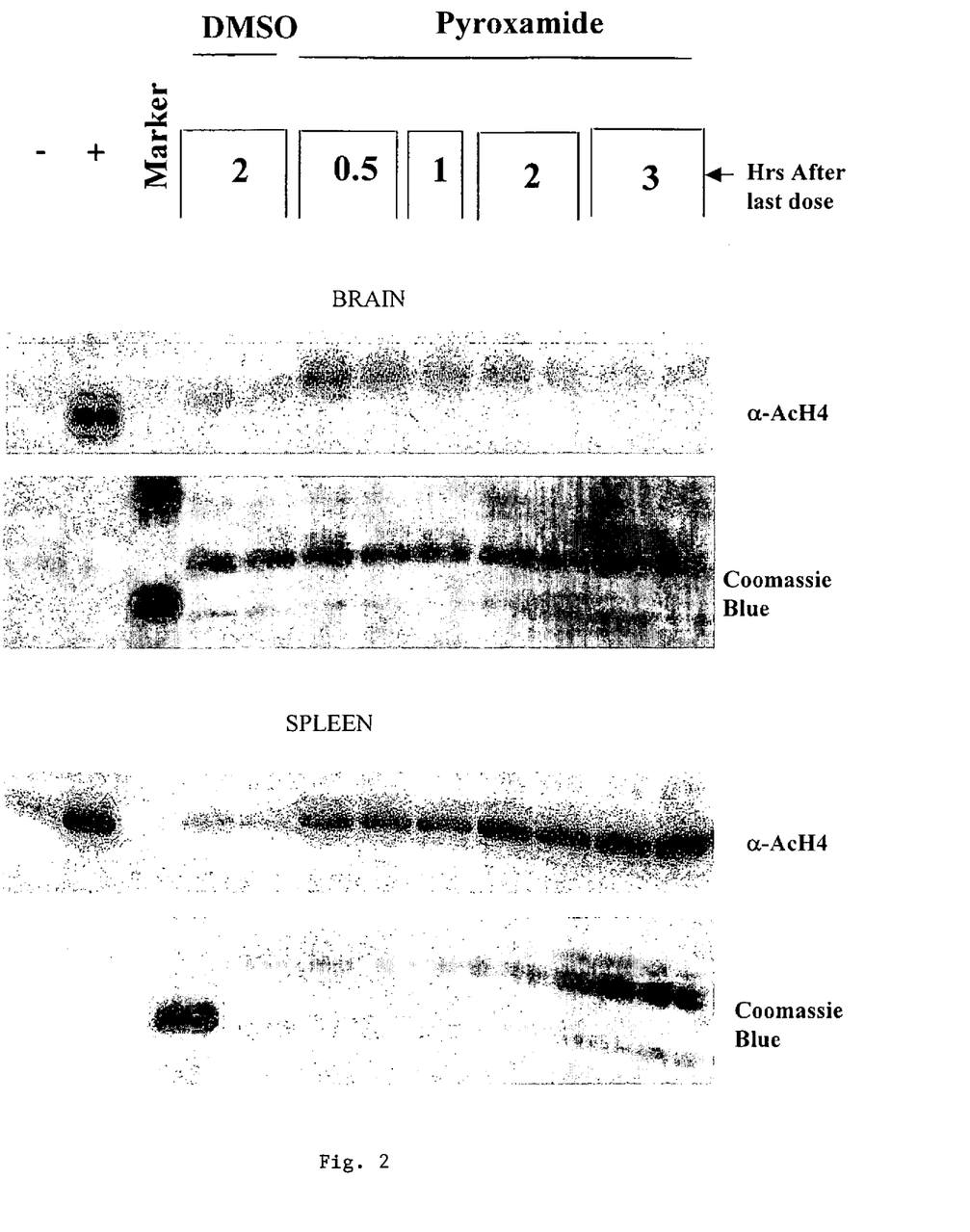
FIG. 2 is a scan of a Western blot and Coomassie stained gel indicating levels of acetylated histone ($\alpha$AcH4) at the indicated timepoints following treatment with vehicle (DMSO) or three doses of Pyroxamide (100 mg/kg/hr).

Mice (2 mice per condition) were injected by intraperitoneal injection (IP) with either SAHA (100 mg/kg), pyroxamide (200 mg/kg), or vehicle (dimethylsulfoxide). Each mouse was administered three injections at the indicated dose at 1 hour intervals. After the final IP injection tissues (brain, spleen or liver) were isolated at the times indicated. Histones were isolated from tissues essentially as described by Yoshida et al., (1990) J. Biol. Chem. 265:17174-17179. Equal amounts of histones (1 µg) were electrophoresed on 15% SDS-polyacrylamide gels and transferred to Hybond-P filters (Amersham). Filters were blocked with 3% milk and probed with a rabbit purified polyclonal anti-acetylated histone H4 antibody (αAc-H4) and anti-acetylated histone H3 antibody (αAc-H3) (Upstate Biotechnology, Inc.). Levels of acetylated histone were visualized using a horseradish peroxidase-conjugated goat anti-rabbit antibody (1:5000) and the SuperSignal chemiluminescent substrate (Pierce). As a loading control for the histone proteins, parallel gels were run and stained with Coomassie Blue (CB). The results are shown in FIGS. 1 and 2.

What is claimed is:

1. A method of treating a brain cancer that is responsive to HDAC inhibition as measured by accumulation of acetylated histones in a mammal in need thereof comprising administering to the mammal a therapeutically effective amount of a histone deacetylase inhibitor compound, wherein the compound comprises Suberoylanilide Hydroxamic Acid (SAHA), represented as:

or a pharmaceutically acceptable salt thereof, wherein brain cancer is effectively treated.

2. The method of claim 1, wherein the histone deacetylase inhibitor compound is administered orally.

3. The method of claim 1, wherein the mammal is a human.

4. The method of claim 1, wherein SAHA is administered.

* * * * *